United States Patent [19]
Aoki et al.

[11] Patent Number: 5,372,838
[45] Date of Patent: Dec. 13, 1994

[54] PROCESS FOR FABRICATING ELECTRODE OF OXYGEN SENSOR

[75] Inventors: Keichiro Aoki, Mishima; Yoshiki Chujo, Susono, both of Japan

[73] Assignee: Toyota Jidosha Kabushiki Kaisha, Aichi, Japan

[21] Appl. No.: 997,195

[22] Filed: Dec. 28, 1992

[30] Foreign Application Priority Data

Dec. 27, 1991 [JP] Japan .................. 3-346437

[51] Int. Cl.$^5$ ............................ C23C 24/00
[52] U.S. Cl. ............................ 427/58; 427/125; 427/126.1; 427/126.3; 427/190; 427/191
[58] Field of Search ........ 427/58, 125, 126.3, 427/126.1, 190, 191

[56] References Cited

U.S. PATENT DOCUMENTS

| | | | |
|---|---|---|---|
| 4,170,531 | 10/1979 | Watanabe | 427/125 |
| 4,225,634 | 9/1980 | Tanaka | 427/125 |
| 5,139,829 | 8/1992 | Minoha | 427/125 |

FOREIGN PATENT DOCUMENTS

| | | |
|---|---|---|
| 57-52852 | 3/1982 | Japan . |
| 57-52853 | 3/1982 | Japan . |
| 57-165758 | 10/1982 | Japan . |
| 58-73857 | 5/1983 | Japan . |
| 61-34456 | 2/1986 | Japan . |
| 61-89160 | 6/1986 | Japan . |
| 61-254848 | 11/1986 | Japan . |
| 1-203964 | 8/1989 | Japan . |
| 3-59454 | 3/1991 | Japan . |

Primary Examiner—Shrive Beck
Assistant Examiner—Vi Duong Dang
Attorney, Agent, or Firm—Oliff & Berridge

[57] ABSTRACT

A process for fabricating an active electrode for an oxygen sensor involves preparing a solution by dissolving an alkoxide of a metal constituting an oxide semiconductor or solid electrolyte in a mixture of a solvent and diethanol amine, adding chloroplatinic acid to said solution to obtain a precipitation, calcining and pulverizing said precipitation to form a micro-composite power of an oxide of said metal and platinum, and forming an electrode on said oxide semiconductor or solid electrolyte using said composite powder.

11 Claims, 4 Drawing Sheets

○ Pt-sputtered electrode
● Pt/zirconia composite electrode

PROCESS FOR FABRICATING ELECTRODE OF OXYGEN SENSOR

BACKGROUND OF THE INVENTION

1. Field of the Invention

The present invention relates to a process for fabricating an electrode for an oxygen sensor.

2. Description of the Related Art

A proposed process for fabricating of an electrode for an oxygen sensor involves mixing stabilized zirconia powders and platinum powders each having a size of 1 μm or less to obtain a paste of a $Pt/ZrO_2$ mixture and baking the same onto stabilized zirconia (Japanese Unexamined Patent Publication (Kokai) No. 57-165758). Compared with a platinum electrode, it is expected that this electrode will have improved adhesion to a solid electrolyte since it contains the same element that is contained in the solid electrolyte, such electrodes will have a higher porosity, an increased specific surface area of platinum, and a three phase interface, thereby permitting the operation of the solid electrolyte at a low temperature.

Nevertheless, since the above process uses a mixture of powders, the fineness and dispersibility of the powders are not high and the possible electrode activity is limited. Further, conventional pastes generally require an inorganic additive such as glass frit, which causes the electrode to coagulate and thus deteriorates the electrode.

The object of the present invention is, therefore, to solve the above problem and to provide a process for fabricating an electrode with activity at a lower temperature and with excellent stability.

SUMMARY OF THE INVENTION

The present invention provides a process for fabricating an electrode for an oxygen sensor, comprising the steps of preparing a solution by dissolving an alkoxide of a metal constituting an oxide semiconductor or solid electrolyte in a mixture of a solvent and diethanol amine, adding chloroplatinic acid to said solution to obtain precipitation, calcining and pulverizing said precipitation to form a composite power of an oxide of said metal and platinum, and forming an electrode on said oxide semiconductor or solid electrolyte using said composite powder.

DESCRIPTION OF PREFERRED EMBODIMENTS

The oxide semiconductor or solid electrolyte of an oxide sensor may be, for example, stabilized zirconia, titanium oxide, silicon oxide, etc.

When oxidized, the metal constituting such an oxide semiconductor or solid electrolyte becomes an oxide having a composition the same or similar to that of the semiconductor or solid electrolyte and, therefore, the electrode material comprising that oxide and platinum will have improved adhesion to the semiconductor or solid electrolyte. Further, if an oxide having the same composition as that of the semiconductor or solid electrolyte is formed by oxidation of the metal, the electrode itself will contain the three phase interface which is more preferred. For example, zirconium and the stabilizing element for a stabilized zirconia, and titanium for titaniumoxide can be considered as the metal to form such an oxide.

The alkoxide of a metal constituting an oxide semiconductor or solid electrolyte may be any available alkoxide, such as propoxide, isopropoxide, ethoxide, butoxide, etc.

The solvent for a metal alkoxide may be any known solvent, typically alcohols such as ethanol, propanol and isopropanol. The concentration of the metal alkoxide is preferably not more than 10% by weight so as to lower the metal ion concentration in the solution and prevent non-uniform precipitation.

The diethanol amine is considered to act as a complexing agent although its exact function is not clear. The concentration of diethanol amine is preferably 4 to 10 times, in moles, the concentration of the total metal alkoxide and chloroplatinic acid which will be added. If the concentration of diethanol amine is too low, the formation of the complex becomes insufficient, and if too much, the complex to be precipitated will be dissolved in the solution.

An example of the preferred mixture of a solvent and diethanol amine is a mixture of ethanol and diethanol amine. The mixing ratio thereof is preferably 3:1 to 5:1 in moles.

Heating is preferably effected to dissolve a metal alkoxide in a mixture of a solvent and diethanol amine. The heating is preferable to accelerate the uniformity of the solution and the formation of a complex but heating is not essential.

Chloroplatinic acid is then added to the mixture solution. It is convenient to add a solution of chloroplatinic acid in a solvent such as ethanol to said mixture solution. The concentration of the chloroplatinic acid in the solution is preferably diluted 10 to 30 times in mole ratio of the solvent.

The mixing ratio of metal alkoxide to chloroplatinum acid is such that the chloroplatinum acid is generally more than 50% by volume, and preferably 80 to 50% by volume. Electric conductivity is necessary for an electrode and platinum should occupy more than 50% by volume to ensure such an electric conductivity, but if platinum acid presents more than 80% by volume, the growth of platinum grains occurs during the calcination, which is disadvantageous.

When chloroplatinic acid is added to a solution of metal alkoxide, a precipitation is obtained, and it is considered that the precipitated product is essentially a micro-composite particle of platinum and metal constituting the metal alkoxide. The precipitation is recovered, for example, by decantation or filtration or the like.

The recovered precipitation product is then calcined to remove the solvent etc. and densify the product. The calcination is generally conducted at a temperature of 600° to 800° C. If the calcination temperature is lower than 600° C., carbon remains and, if above 800° C., platinum particles sinter. The atmosphere for the calcination may be an oxidizing atmosphere, usually in the air.

The calcined products are then pulverized to form composite powders having a particle size of, for example, 0.05 to 6.0 μm. Preferably, the particle size of the composite powders is less than 1.0 μm, or the average particle size of the composite powders is from 0.5 to 1.0 μm.

The thus obtained composite powders are mixed with an adequate binder, for example, ethyl cellulose, coated and baked onto a sensor portion of an oxide semiconductor or solid electrolyte to form an electrode. Since the composite powders are very similar to the oxide semiconductor or solid electrolyte in composition and/or structure and are fine in size, they can be baked or fired without an inorganic compound such as glass frit. The binder is not essential and a viscous liquid may be used. The baking temperature is generally in a range of 800° to 1200° C.

Since the composite of platinum and an oxide of a metal constituting an oxide semiconductor or solid electrolyte is formed by coprecipitation, the obtained precipitation is a micro scale and finely dispersed porous composite powder of a metal oxide (the same as or similar to the oxide semiconductor or solid electrolyte in composition) and platinum, which provides a highly active electrode by increasing the specific surface area of the platinum electrode and, further, increasing the three phase interface if the metal oxide is the same composition as that of the oxide semiconductor or solid electrolyte. Adhesion of the electrode to the oxide semiconductor or solid electrolyte is also improved and stability of the electrode is provided.

EXAMPLES

EXAMPLE 1

Ethanol and diethanol amine were mixed in a volume ratio of 50:1, to which 0.103 g ($3 \times 10^{-4}$ mole) of zirconium tetrapropoxide $Zr(O-C_3H_7)_4$ and 0.01 g ($2.6 \times 10^{-5}$ mole) of yttrium triisopropoxide $Y(O-iC_3H_7)_3$ were added and heated to 40° C. to dissolve the latter in the former.

To this zirconium tetrapropoxide solution, a solution in which 1 g (0.002 mole) of chloroplatinum acid $H_2PtCl_6.6H_2O$ had been dissolved in 10 ml of ethanol was dropwise added. The precipitation obtained in the solution by this dropwise addition was separated and recovered by decantation for 12 to 24 hours.

The recovered precipitation was calcined in the air at 600° C. and the calcined product was crushed in a mortar.

The thus obtained powders had a particle size distribution of 0.09 to 5.87 $\mu$m and an average particle size of 0.933 $\mu$m.

The powders were mixed with an organic binder, etc., coated onto a solid electrolyte of a stabilized zirconia, dried, and fired at 1000° C. to form an electrode.

Figure 1A:
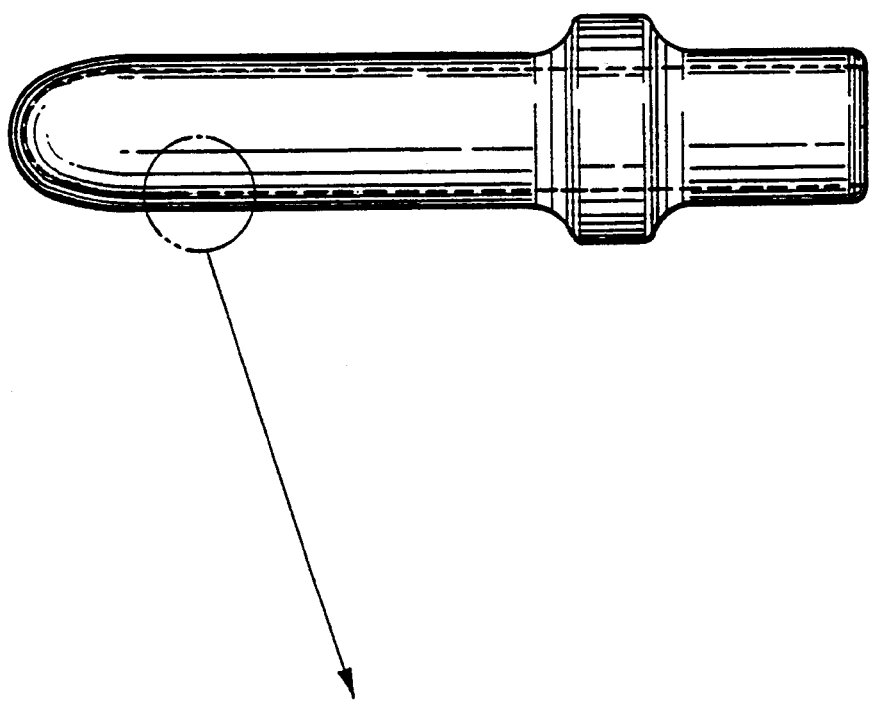
FIGS. 1A and 1B schematically show an oxygen sensor element.
Figure 1B:
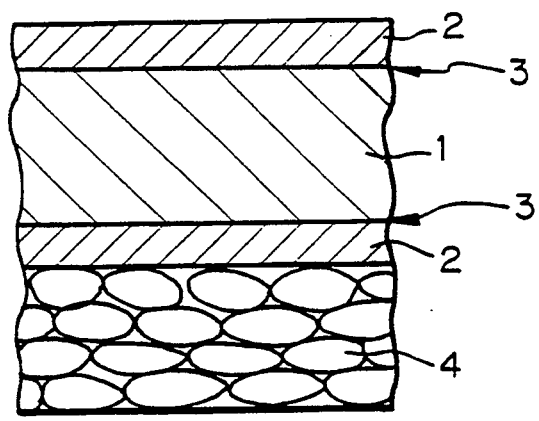

FIG. 1A shows the shape of the fabricated oxygen sensor element and FIG. 1B shows an enlarged vertical section of a part of a wall of the oxygen sensor element in which 1 denotes a solid electrolyte, 2 a composite electrode, 3 an interface of the solid electrolyte 1 and the composite electrolyte 2, and 4 a coating.

Figure 2A:
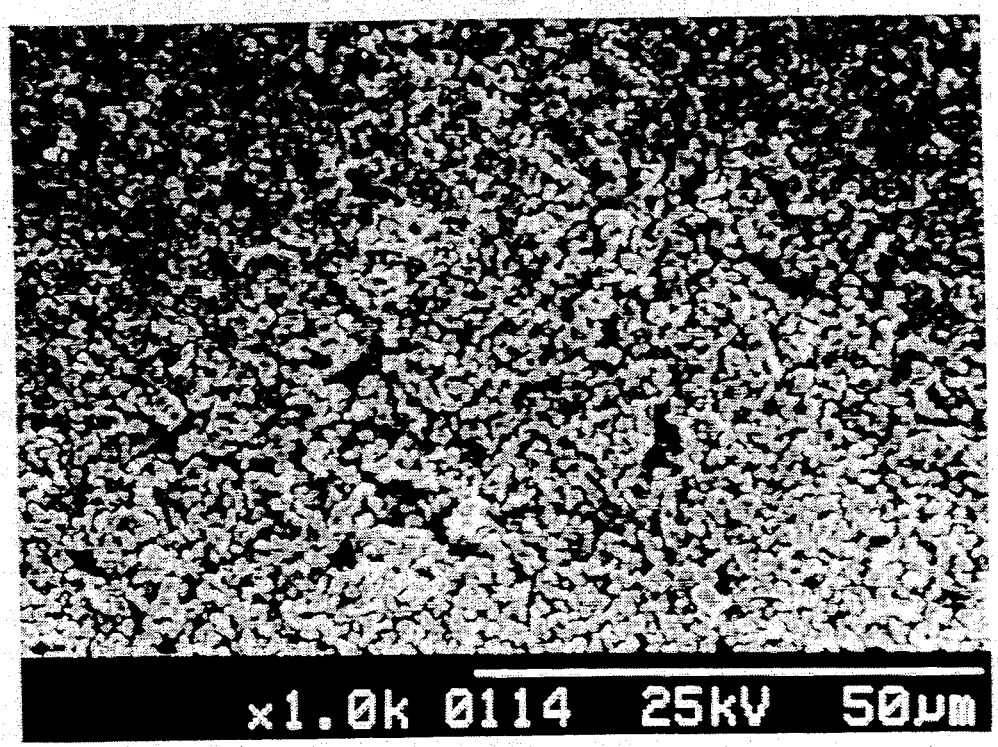
FIGS. 2A and 2B are SEM photographs at different magnification of a fired electrode made from a composite powder of a metal oxide and platinum in Example 1.
Figure 2B:
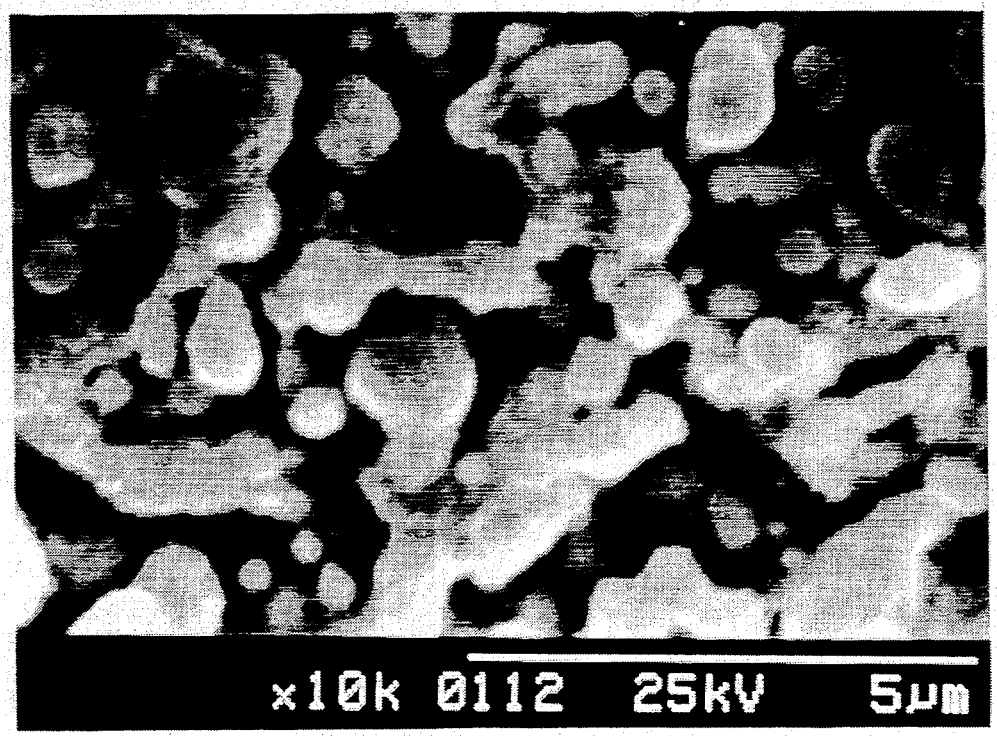

FIGS. 2A and 2B are microphotographs of the same fired electrode provided by a scanning electron microphotography (SEM) at different magnifications.

By applying a voltage to this oxygen sensor, an overpotential was measured between the cathode and the solid electrolyte. The thus obtained relationships between the current density and the overpotential are shown in FIG. 3.

For comparison, a conventional oxygen sensor of the same stabilized zirconia as the above was made by sputtering platinum onto the stabilized zirconia and the characteristics thereof were measured. The results are also shown in FIG. 3.

Figure 3:
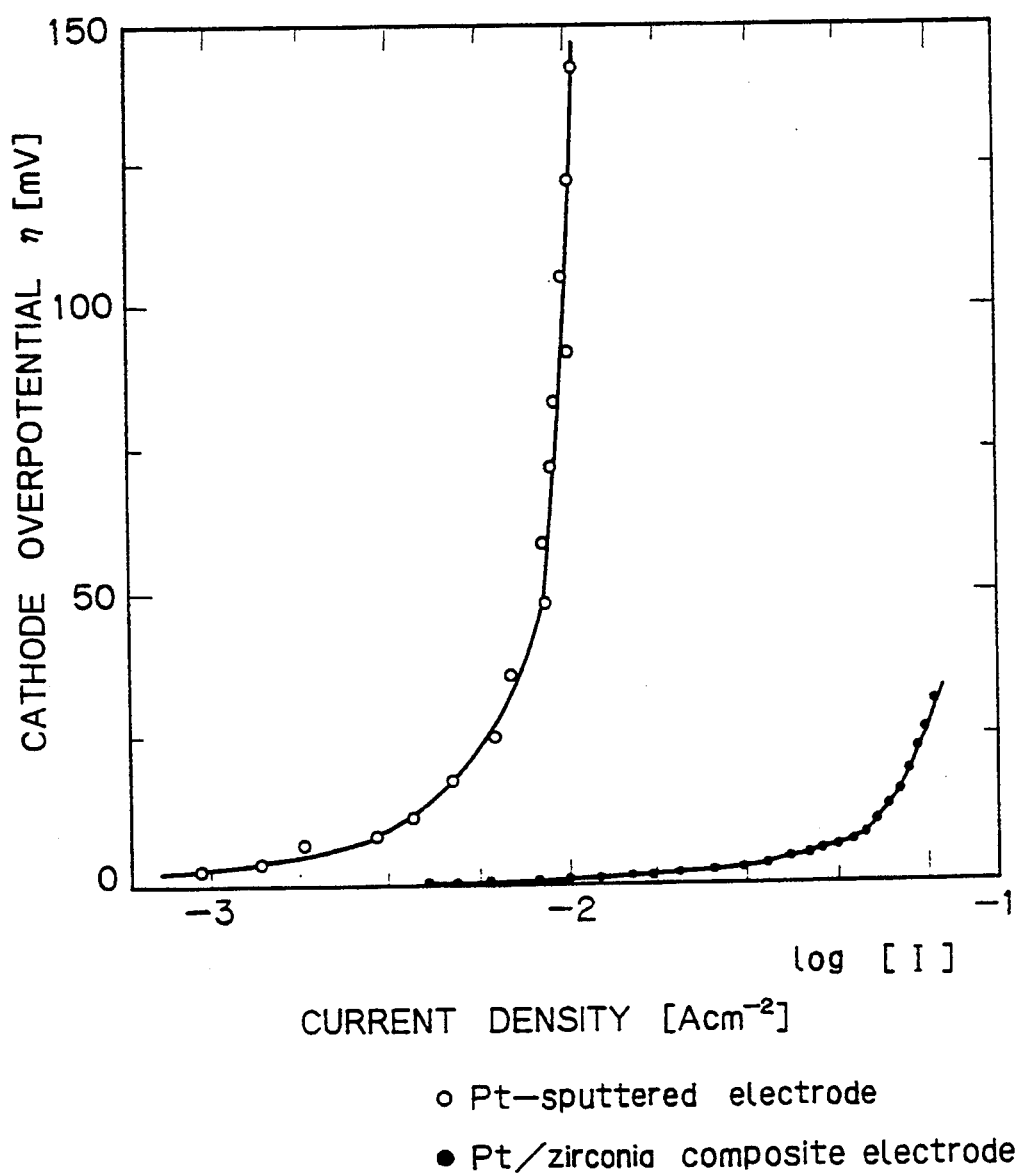
FIG. 3 shows the cathode overpotentials of oxygen sensors in Example 1 and a Comparative example.

As seen in FIG. 3, the overpotential of the oxygen sensor of Example 1 is far lower than that of the conventional oxygen sensor. This clearly indicates that adhesion of the electrode to the electrolyte was high and there were a lot of reaction active points in the electrode.

EXAMPLE 2

Ethanol and diethanol amine were mixed in a volume ratio of 50:1, to which 0.076 g ($2.7 \times 10^{-4}$ mole) of titanium tetraisopropoxide $Ti(O-iC_3H_7)_4$ was added and heated to 40° C. to form a solution thereof.

To this titanium tetraisopropoxide solution, a solution in which 1 g (0.002 mole) of chloroplatinum acid $H_2PtCl_6.6H_2O$ had been dissolved in 10 ml of ethanol was dropwise added. The precipitation obtained in the solution by this dropwise addition was separated and recovered by decantation for 12 to 24 hours.

The recovered precipitation was calcined in the air at 600° C. and the calcined product was crushed in a mortar.

In the same manner as in Example 1, the obtained powders were mixed with an organic binder, etc., coated onto a solid electrolyte of stabilized zirconia, dried, and fired at 1000° C. to form an electrode.

The thus obtained oxygen sensor had characteristics very similar to those of Example 1.

We claim:

1. A process for fabricating an electrode for an oxygen sensor, comprising the steps of:
   preparing a solution by dissolving an alkoxide of a metal constituting an oxide semiconductor or solid electrolyte in a mixture of a solvent and diethanol amine,
   adding chloroplatinic acid to said solution to obtain a precipitation,
   calcining and pulverizing said precipitation to form a composite powder of an oxide of said metal and platinum, and
   coating said composite powder onto a sensor portion of an oxide semiconductor or solid electrolyte and baking said composite powder to form an electrode.

2. A process according to claim 1 wherein said oxide semiconductor or solid electrolyte is selected from the group consisting of stabilized zirconia, titanium oxide and silicon oxide.

3. A process according to claim 1 wherein said metal constituting an oxide semiconductor or solid electrolyte is selected from the group consisting of Zr, Ca and Ti.

4. A process according to claim 1 wherein said alkoxide is selected from the group consisting of propoxide, isopropoxide, ethoxide and butoxide.

5. A process according to claim 1 wherein said metal alkoxide has a concentration of not more than 10% by weight in the mixture of a solvent and diethanol amine.

6. A process according to claim 1 wherein said diethanol amine is used in an amount of 4 to 10 times, in moles, that of the total of metal alkoxide and chloroplatinic acid to be added.

7. A process according to claim 1 wherein said mixture of a solvent and diethanol amine has a mixing ratio of 3:1 to 5:1 in mole.

8. A process according to claim 1 wherein said chloroplatinic acid is in the form of a solution of chloroplatinic acid in ethanol.

9. A process according to claim 8 wherein said chloroplatinic acid solution is diluted 10 to 30 times in mole ratio of said ethanol.

10. A process according to claim 1 wherein said chloroplatinic acid is mixed with the metal alkoxide in such a ratio that the chloroplatinic acid is 80 to 50% by volume.

11. A process according to claim 1 wherein said composite powder has an average particle size of 0.5 to 1.0 μm.

* * * * *